(12) United States Patent
Borysow et al.

(10) Patent No.: US 8,111,394 B1
(45) Date of Patent: Feb. 7, 2012

(54) RAMAN SPECTROMETER FOR MONITORING TRACES OF DISSOLVED ORGANIC AND INORGANIC SUBSTANCES

(75) Inventors: Jacek Borysow, Atlantic Mine, MI (US); Manfred Fink, Austin, TX (US); Philip Varghese, Austin, TX (US)

(73) Assignee: IsoSpec Technologies, LP, Houston, TX (US)

( * ) Notice: Subject to any disclaimer, the term of this patent is extended or adjusted under 35 U.S.C. 154(b) by 0 days.

(21) Appl. No.: 13/078,777

(22) Filed: Apr. 1, 2011

(51) Int. Cl.
*G01J 3/44* (2006.01)
(52) U.S. Cl. ........................................ 356/301
(58) Field of Classification Search .................. 356/301
See application file for complete search history.

(56) References Cited

U.S. PATENT DOCUMENTS

2003/0081206 A1* 5/2003 Doyle ............................ 356/301

OTHER PUBLICATIONS

Pushkarsky et al. "High-sensitivity detection of TNT." PNAS vol. 103 No. 52 (Dec. 26, 2006) pp. 19630-19634.
Taylor et al. "Enhanced Raman sensitivity using an actively stabilized external resonator," Review of Scientific Instruments, vol. 72 No. 4 (Apr. 2001) pp. 1970-1976.
Borysow et al. "NIR Raman spectrometer for monitoring protonation reactions in gaseous hydrogen." Journal of Nuclear Materials 341 (2005) pp. 224-230.
Habuka et al. "Rate Theory of Multicomponent Adsorption of Organic Species on Silicon Wafer Surface." Journal of the Electrochemical Society, 147 (6) (2000) pp. 2319-2323.
Robinson et al. "New vapor phase spontaneous Raman spectrometer." Rev. Sci. Instrum. 63 (6) Jun. 1992, pp. 3280-3284.
Sabbaghzadeh et al. "A very narrow, high throughput Rayleigh filter for Raman spectroscopy," Appl. Phys. B 60, S261-S265 (1995).
Kiefer et al. "The Vapor-Phase Raman Spectra and the Ring-Puckering Vibration of Some Deuterated Analogs of Trimethylene Oxide." Journal of Molecular Spectroscopy 43, 393-400 (1972).

* cited by examiner

*Primary Examiner* — Tarifur Chowdhury
*Assistant Examiner* — Abdullahi Nur
(74) *Attorney, Agent, or Firm* — Hulsey, P.C.; William N. Hulsey, III; Loren T. Smith

(57) ABSTRACT

A compact, ultra-sensitive, inexpensive NIR spontaneous Raman spectrometer is presented. High sensitivity is achieved by the use of a multi-pass cell configuration combined with the electromotive properties of silicon crystal surface. A thin layer of silicon oxide chemisorbs molecules, which stick to its surface without altering their spectroscopic signatures. This new Raman spectrometer may be used to detect less than 40 ng (≈0.5 n mol) of ammonium nitrate deposited on the silicon surface with the signal-to-noise ratio better than 50 during 0.1 s recording time and for an illuminated area of $2 \times 10^{-8}$ $m^2$. These results may be useful in many areas, for example the foundation of an extended project to record the dissolved $NO_3^-$ ions in a large river such as the Mississippi.

13 Claims, 3 Drawing Sheets

RAMAN SPECTROMETER FOR MONITORING TRACES OF DISSOLVED ORGANIC AND INORGANIC SUBSTANCES

FIELD

Provided is a Raman spectral analyzer to measure the scattered light from a multi-pass Raman cell. More specifically, a Raman spectral analyzer capable of measuring trace amounts of compounds on a silicon wafer is provided.

BACKGROUND

Raman scattering is a type of inelastic scattering of electromagnetic radiation, such as visible light, discovered in 1928 by Chandrasekhara Raman. When a beam of monochromatic light is passed through a substance some of the radiation will be scattered. Although most of the scattered radiation will be the same as the incident frequency ("Rayleigh" scattering), some will have frequencies above ("anti-Stokes" radiation) and below ("Stokes" radiation) that of the incident beam. This effect is known as Raman scattering and is due to inelastic collisions between photons and molecules that lead to changes in the vibrational and/or rotational energy levels of the molecules. This effect is used in Raman spectroscopy for identifying and investigating the vibrational and rotational energy levels of molecules. Raman spectroscopy is the spectrophotometric detection of the inelastically scattered light.

"Stokes" emissions have lower energies (lower frequencies or a decrease in wave number ($cm^{-1}$)) than the incident laser photons and occur when a molecule absorbs incident laser energy and relaxes into an excited rotational and/or vibrational state. Each molecular species will generate a set of characteristic Stokes lines that are displaced from the excitation frequency (Raman shifted) whose intensities are linearly proportional to the density of the species in the sample.

"Anti-Stokes" emissions have higher frequencies than the incident laser photons and occur only when the photon encounters a molecule that, for instance, is initially in a vibrational excited state due to elevated sample temperature. When the final molecular state has lower energy than the initial state, the scattered photon has the energy of the incident photon plus the difference in energy between the molecule's original and final states. Like Stokes emissions, anti-Stokes emissions provide a quantitative fingerprint for the molecule involved in the scattering process. This part of the spectrum is seldom used for analytical purposes since the spectral features are weaker. However, the ratio of the Stokes to the anti-Stokes scattering can be used to determine the sample temperature when it is in thermal equilibrium.

The Stokes and anti-Stokes emissions are collectively referred to as spontaneous Raman emissions. Since the excitation frequency and the frequency of the Stokes (and anti-Stokes) scattered light are typically far off the excitation of any other component in the sample, fluorescence in near infrared (NIR) wavelengths is minimal. The sample is optically thin and will not alter the intensities of the Stokes emissions (no primary or secondary extinctions), in stark contrast to infrared spectroscopy.

Raman spectroscopy is a well-established technology to determine the presence of trace compounds down to very low (e.g. n mol/liter) levels. With Raman analysis, absolute densities can be determined, the sparse spectra minimize interferences, and overtones and combination lines are strongly suppressed.

However, conventional Raman analyzers tend to lack the desired sensitivity, require an extensive integration time, be too large, and/or be too costly for widespread use. Thus, there is a need in the art for a relatively inexpensive, compact Raman spectrometer capable of improved sensitivity and integration times.

Laser-based techniques capable of detecting very small traces of inorganic compounds have been recently reported in the literature. However, these instruments generally require the use of tunable lasers and special environments like a vibration-free setting. Often the experimental setups are so sophisticated that they can be operated only by Ph.D. level personnel.

A novel approach is presented here. Raman spectroscopy is often used for identification and quantization of a mixture of chemical species with high selectivity. In a typical Raman experiment, a laser is used as an excitation source. Scattered light is collected and sent to a grating spectrograph connected to a detector, typically a charge-coupled device (CCD). Elastically scattered (Rayleigh) light is rejected by a narrow atomic vapor filter.

There are many Raman systems on the market today; however, they tend to suffer from the same drawbacks. Raman cross sections are extremely small; therefore, only dense materials (solids or liquids) in sufficiently large quantities can be routinely detected by these instruments. Raman spectrometers capable of detecting low densities of gaseous substances have been reported in elaborate intra-cavity laser setups, but these techniques require sophisticated frequency stabilization and can be achieved today only in state-of-the-art laboratories, without much hope for deployment in the field.

SUMMARY

We have recently presented a Raman spectrometer capable of differentiating isotopes of hydrogen at densities as low as $5 \times 10^{13}$ $cm^{-3}$ (see J. Borysow and M. Fink, "NIR Raman Spectrometer for Monitoring Protonation Reactions in Gaseous Hydrogen," J. Nucl. Mat, 341: 224-230 (2005)). The high sensitivity was achieved using a multi-pass cell in conjunction with an atomic vapor Rb absorption filter, which eliminates the Rayleigh, scattered light. Similar sensitivities are possible for molecules dissolved in transparent liquids such as water. However, the vapor pressures of many organic solids such as polycyclic ether, natural products, or nitrates at room temperature are significantly lower than this detection limit. Therefore, that spectrometer may have difficulty detecting these compounds.

The design we present here takes advantage of the ability of the oxidized silicon wafer surface to attract via electrostatic forces a large variety of organic and inorganic molecules. The presence and the rates of adsorption and desorption of organic molecules (especially hydrocarbons) have been studied because they may cause serious problems in the advanced electronics fabrication processes.

However, even today relatively little is known about the interactions of the vapors of many inorganic compounds with silicon surfaces. When the sticking coefficients for these species on silicon wafers are as high as for most organic hydrocarbons, $SiO_2$ is an extremely efficient collection element. The Raman spectrometer design described here may reach detection limits of n mol/liter for ammonium nitrate ($NH_4NO_3$ or AN), the primary compound used in this study.

Our approach may lead to the development of systems that can measure a large variety of molecules in short order and calibrated to an absolute scale over a very large dynamic range. Traces of AN deposited on the silicon wafer surface have been recorded to demonstrate the performance of our novel Raman set-up. The measurements of the densities of AN in a river, such as the Mississippi, can be very useful for the evaluation of data collected in research projects which focus on the environment.

Nitrate compounds are routinely used as fertilizers. An appreciable amount is transferred by the weather to the local tributaries. Our Raman spectrometer is rugged and affordable enough that one could, for example, equip a high school in every district on the river with a Raman instrument and ask the students to record the daily changes of AN for extended time periods to establish seasonal and temporal variations.

Additional advantages will be set forth in part in the description which follows, and in part will be obvious from the description, or may be learned by practice of the aspects of the disclosure as described herein. The advantages can be realized and attained by means of the elements and combinations particularly pointed out in the appended claims. It is to be understood that both the foregoing general description and the following detailed description are exemplary and explanatory only and are not restrictive of the aspects of the disclosure, as claimed.

BRIEF DESCRIPTION OF THE DRAWINGS

The features, nature, and advantages of the disclosed subject matter will become more apparent from the detailed description set forth below when taken in conjunction with the accompanying drawings, wherein.

DETAILED DESCRIPTION

The present disclosure may be understood more readily by reference to the following detailed description, examples, drawings, and claims, and their previous and following description. However, before the present devices, systems, and/or methods are disclosed and described, it is to be understood that this disclosure is not limited to the specific devices, systems, and/or methods disclosed unless otherwise specified, as such can, of course, vary. It is also to be understood that the terminology used herein is for the purpose of describing particular aspects only and is not intended to be limiting.

As used in the specification and the appended claims, the singular forms "a," "an" and "the" include plural referents unless the context clearly dictates otherwise. Thus, for example, reference to an "analyzer" can include two or more such analyzers unless the context indicates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

As used herein, the terms "optional" or "optionally" mean that the subsequently described event or circumstance may or may not occur, and that the description includes instances where said event or circumstance occurs and instances where it does not.

Reference will now be made in detail to certain embodiments of the disclosure, examples of which are illustrated in the accompanying drawings. Wherever possible, the same reference numbers are used throughout the drawings to refer to the same or like parts.

Figure 1:
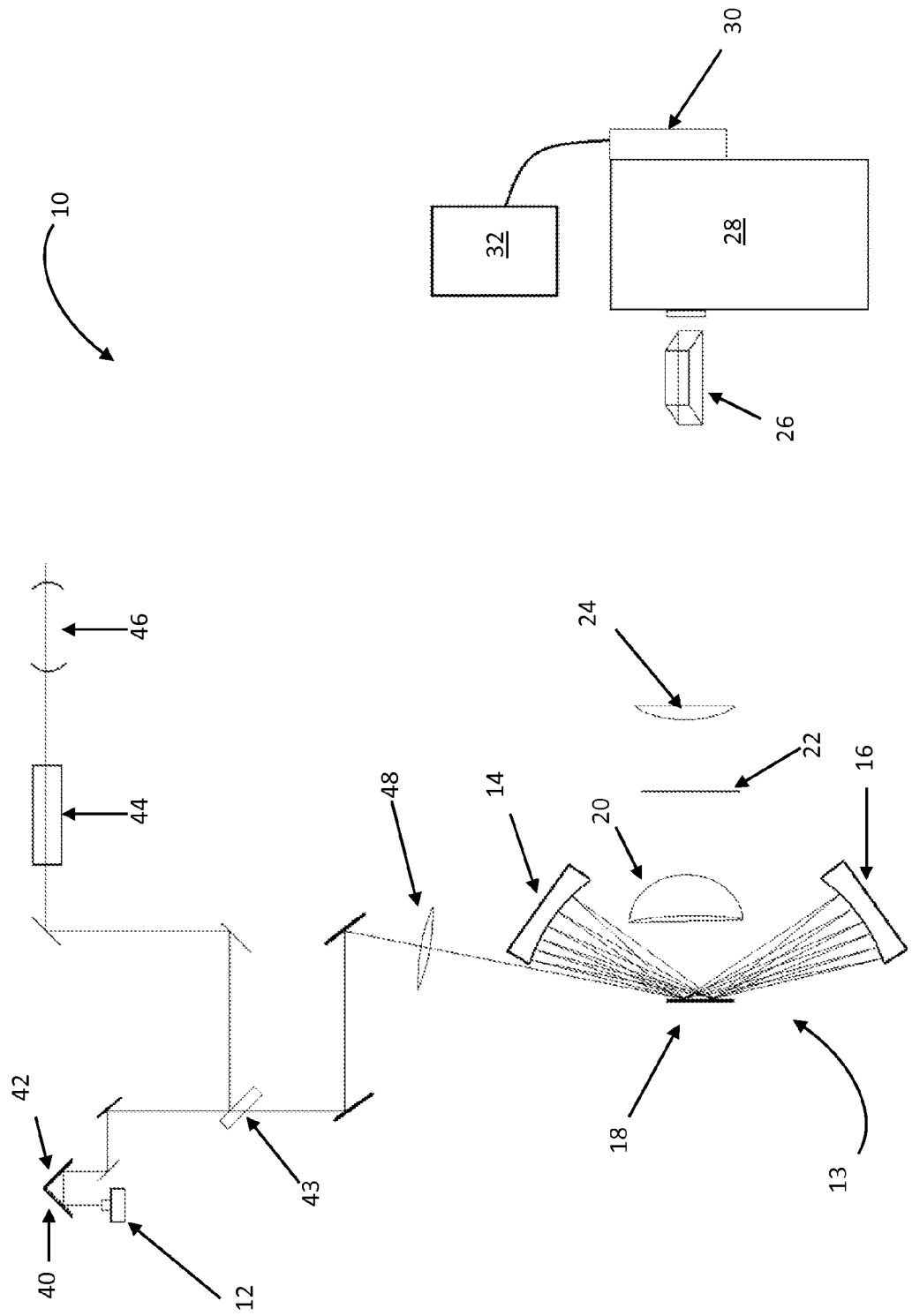
FIG. 1 is a schematic drawing of one embodiment of the multi-pass Raman cell of the present disclosure.

A Raman apparatus in accordance with the present disclosure is illustrated in FIG. 1. The main components are as follows. Raman apparatus 10 includes laser diode 12 tuned to the D2 line of rubidium (Rb) near 780 nm. Light from laser diode 12 is directed into multi-pass cell 13, which is formed by concave mirrors 14 and 16. In one embodiment, mirrors 14 and 16 are 50.2-mm diameter concave mirrors with a 100.0 mm radius of curvature, and they may be made out of BK7 glass or any other suitable material. The concave mirrors are shown to be separated by a distance of about 200 mm. One of ordinary skill will recognize that multi-pass cell 13 may be formed by any suitable combination of mirror focal length and separation. In one embodiment, the nominal reflectivity of the mirrors at normal incidence is better than 99.99%. Wafer 18 forms the third component of multi-pass cell 13. In one embodiment, wafer 18 may be a polished, N-doped silicon wafer with a native layer of oxide. However, one of ordinary skill will recognize that the doping of the silicon wafer is irrelevant to the present disclosure. P-doped or undoped wafers may also be used without departing from the spirit of this disclosure. The oxide layer is useful for chemisorbing the species to be measured.

Condenser 20 concentrates the Raman scattered light from wafer 18 and passes it through a filter to remove the Rayleigh scattered light. In this embodiment, the filter used is holographic notch filter 22, which has an optical density of at least approximately 5 at the Rayleigh wavelength. In order to detect different compounds, the filter may be swapped out with a different filter or atomic vapor (e.g. Rb) absorption cell as appropriate for the wavelength desired. The Raman light then passes through collecting lens 24, which focuses it down to spectrograph 28, which in this embodiment is a 0.275-m spectrograph. If necessary, the image of the focused light may be rotated by Dove prism 26 in order to bring it parallel to the entrance slit of spectrograph 28. Spectrograph 28 is coupled to CCD camera 30, which may be cooled to reduce noise. CCD camera 30 is coupled to computer 32 for data recording.

As shown in FIG. 1, laser diode 12 may be set up in a grating-locked configuration to ensure that its output has a desirable narrow bandwidth. In this embodiment, the tunable laser diode system is composed of an approximately 6 cm laser cavity is shown with a laser diode (SHARP GH0781JA2C, power of 120 mW in this embodiment) coupled to a collimating lens, with diffraction grating 40 providing the optical feedback. In this embodiment, grating 40 has 1200 grooves/mm blazed at 750 nm and is mounted in the Littrow configuration with the O-order used as the laser output. Mirror 42 mounted at a right angle next to the diffraction grating compensates for horizontal beam displacement caused by grating rotation during tuning. The temperature of the laser diode may be kept constant by a thermoelectric cooler (not shown). Once tuned to the frequency of the rubidium D2 line, the laser drift may be less than 1.0 GHz per hour without an active frequency locking mechanism.

A portion of the laser light may be picked off by beam splitter 43 and then used for frequency tuning. The fluorescence monitored by the infrared viewer from rubidium reference cell 44 may be used to tune the laser to Rb D2 line. The mode structure may be monitored by scanning confocal Fabry-Perot interferometer 46, which has a 7.5 GHz free spectral range and a finesse of 200. The laser diode may be powered by a standard commercial current source. The estimated power of the monochromatic light in this embodiment is about 40 mW. The laser light may be polarized vertically to the table plane.

In actual operation of the system, beam splitter 43 and the other components used for frequency tuning may be omitted once the system has reached a stable state.

Lens 48, a 120-mm focal length convex lens is placed such that it focuses the laser onto the silicon surface at a nearly grazing angle. The beam then diverges and is re-focused to nearly the same place several times by mirrors 16 and 14. After each subsequent reflection, the angle of incidence at the silicon surface decreases together with the fraction of laser light entering the silicon (i.e. refracted light). The refracted laser light is essentially completely absorbed in the silicon. The estimated increase of the light intensity at the target in the multi-pass configuration and the consequent increase in Raman signal is nearly a factor of 5 compared to a single pass. Silicon's index of refraction at 780 nm is assumed to be equal to 3.70, and the well-known Fresnel equations may be to compute the intensity of the reflected light as a function of the angle of incidence.

The Raman scattered light is collected by condenser 20, which in this embodiment is a multi-element uncoated condenser lens made of borosilicate crown glass, with f/#0.7 and with a back focal length of about 25 mm. Lens 24, a 50-mm diameter and 200-mm focal length lens, images the scattering volume to the entrance slit of spectrograph 28, a 0.275-m Turner-Czerny spectrograph in this embodiment. The light image is rotated by 90° in this embodiment by Dove prism 26 before entering the spectrograph. This arrangement images approximately 20 micron×0.8 mm of a focused laser beam area on the silicon wafer onto the 160 micron×6 mm entrance slit of the spectrograph. The imaging optics match closely the f/#4 number of the spectrograph. The overall magnification of the collection optics is about 8. The grating used in all measurements has 600 grooves/mm and is blazed at 1.0 micron. The resulting resolution is 0.2 nm (or 3.2 cm$^{-1}$). A back-illuminated, cooled (243 K) Hamamatsu CCD array with 1024×256 24-micron pixels with a well capacity of 300,000 electrons per pixel may be used as a light detector. The dark electron count at 243 K in this embodiment is about 10 electrons per pixel per second. Most spectra were taken with an exposure time between 0.01 s and 1.0 minute.

To prepare the wafer for testing detection of AN, solid AN may be dissolved in water or methanol with a concentration of 43 g/liter. Then a pre-measured drop of the solution, approximately 1/37 ml, is applied to the silicon to cover a surface area of about 1.7×1.7 cm$^2$. The resulting surface density of AN is 2.9×10$^{22}$ molecules/m$^2$ or about 1000 monolayers of NH$_4$NO$_3$, calculated from the specific density of 1.725 gr/cm$^3$. The area where the laser beam interacts with the NH$_4$NO$_3$, with micro crystalline AN is estimated to be 2.0× 10$^{-8}$ m$^2$. We assume that the laser is operating in TEM00 mode and characterized by the Gaussian intensity distribution. Assuming a uniform distribution of AN on the surface of silicon, we conclude that the excitation laser light interacted with about 4.5×10$^{14}$ molecules or 0.5 n mol of AN.

The pre-measured, dissolved AN used in this embodiment has advantages for characterizing the sensitivity of the apparatus; however, because of the propensity for molecules to stick to the SiO$_2$ surface, the apparatus may also be used by simply passing a vapor over the SiO$_2$. This allows the device to be used in the field to detect trace amounts of airborne compounds without putting them into a solid or a liquid phase.

Figure 2:
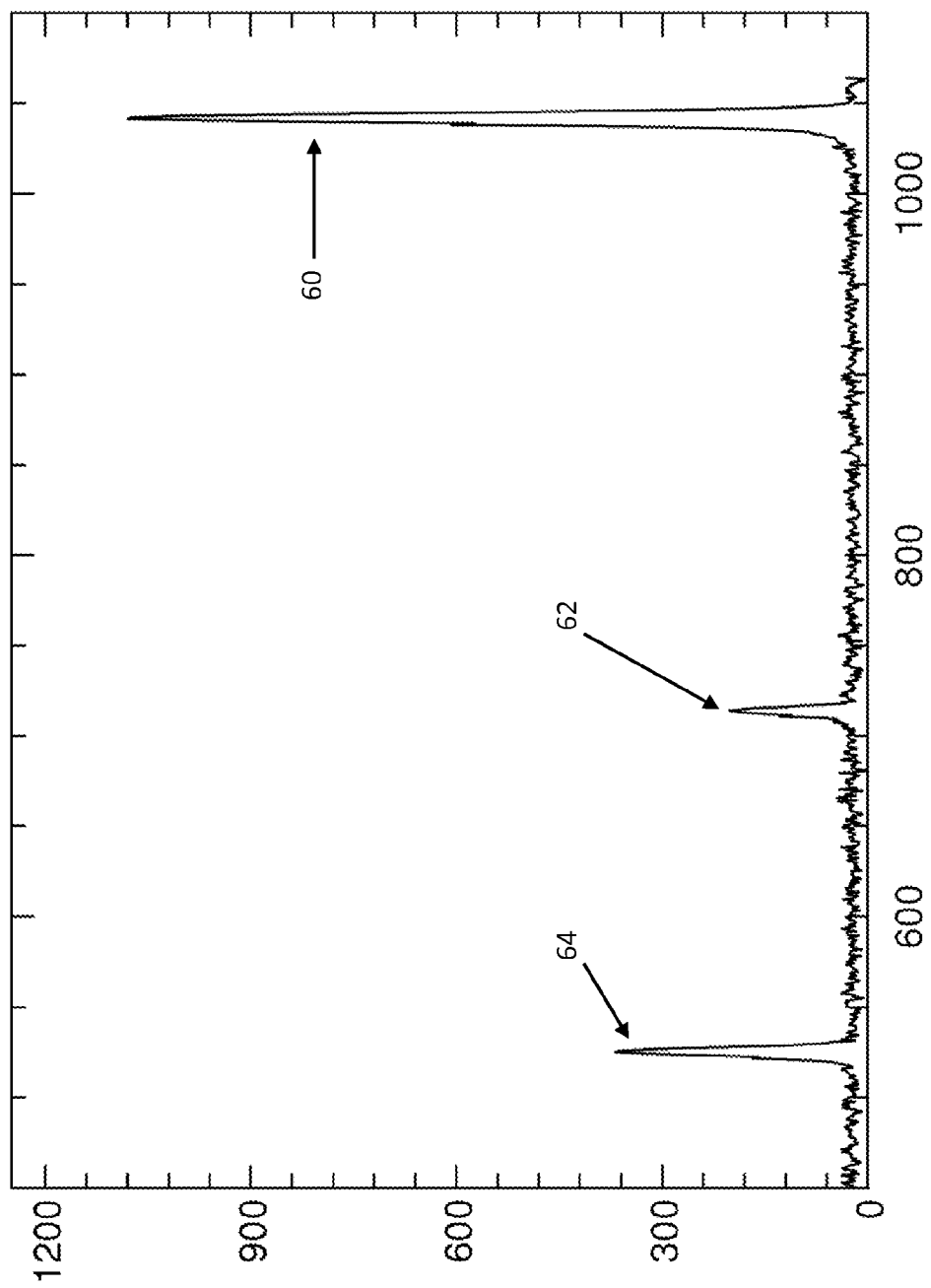
FIG. 2 shows a spectrum of ammonium nitrate measured in accordance with the present disclosure.

The representative Raman spectrum of deposited AN on the silicon surface and obtained with our apparatus is shown in FIG. 2, with Raman shift in cm$^{-1}$ on the x-axis and arbitrary units on the y-axis. The spectrum was taken in open air at room temperature of about 295 K and relative humidity near 70%. The spectrum shown in FIG. 2 is not corrected for response function of the spectrograph and CCD camera. The identification of the nitrate spectral lines 60 and 62 is according to known references for phase III of AN. The unfiltered remnants of Rayleigh line at 780 nm were outside the active area of the CCD detector, but spectral line 64 corresponds to the silicon wafer. The background was subtracted to bring the baseline to zero counts.

Figure 3:
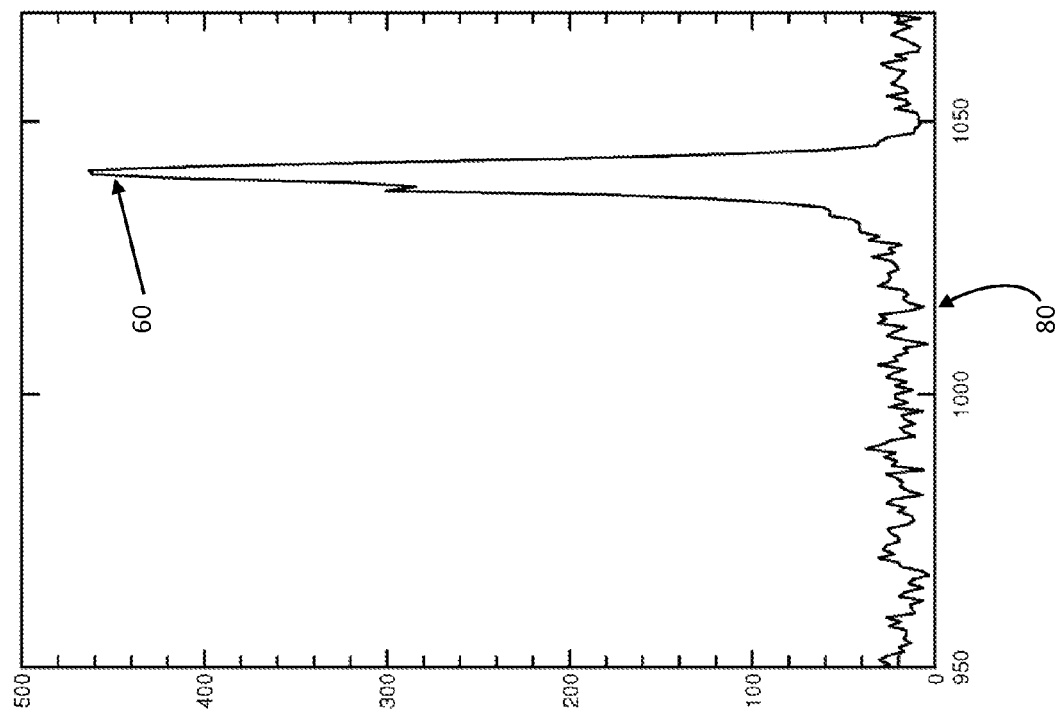
FIG. 3 shows two spectra of ammonium nitrate demonstrating the advantage of using the multi-pass configuration of the present disclosure.
Figure 3:
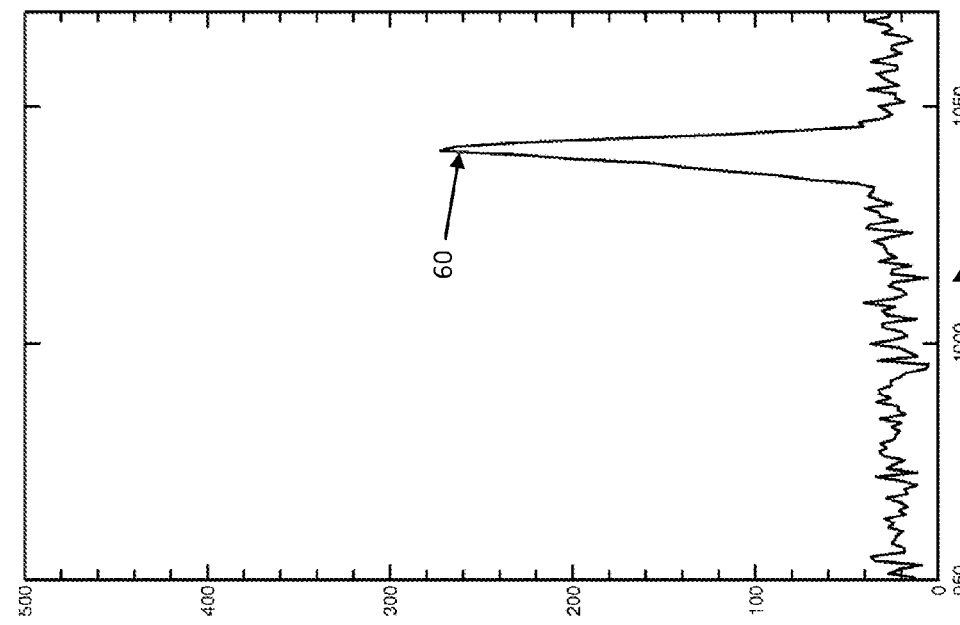

The advantage of using a multi-pass configuration is demonstrated in FIG. 3, with Raman shift in cm$^{-1}$ on the x-axis and arbitrary units on the y-axis, spectrum 70 was taken with a single laser pass with mirror 16 removed. Spectrum 80 was obtained with a double pass configuration with mirror 16 in place and mirror 14 removed. As shown, nearly a 70% increase in the magnitude of Raman signal from AN after the second pass was evident. The increments in Raman line intensity from subsequent passes decreases rapidly with increasing angle of incidence for each subsequent pass due to the decrease in intensity of the reflected laser light.

The estimated signal-to-noise ratio for the strongest line in FIG. 2, spectral line 60, is better than 50. Based on our estimates there were approximately 1000 layers of AN on the surface of the silicon. This translates to a signal-to-noise ratio of 1 (a value usually defined as the detection limit) for 20 layers of NH$_4$NO$_3$.

Under one embodiment of experimental conditions (very short integration times) the shot noise determines the noise level. Thus increasing observation time from 0.01 s to 1 minute lowers the noise level by factor of 70 and brings the detection limit to about ¼ of a monolayer of deposited AN on the silicon.

The present disclosure provides a simple, relatively inexpensive Raman spectrometer as a monitor for traces of molecular species attached to the surface of silicon. We used AN as an example of the capabilities of the spectrometer. AN is a common component of fertilizers, and this disclosure demonstrates that with this spectrometer the sub-monolayer densities of molecules can be detected. It should be straightforward to extend this research to dissolved NO$_3^-$. The substrate may be replaced by a gold plated disk with plasma discharged deposited SiO$_2$ (50 nm). This will significantly increase the laser power in the multi-pass cell. A known amount of solvent may be deposited on a SiO$_2$ substrate, the solvent will evaporate, and the remaining NO$_3^-$ density will be recorded. The unit can be routinely calibrated with AN.

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:
1. A Raman spectrometer comprising:
a laser source emitting a laser beam;
a lens having a lens focal length and being disposed approximately one lens focal length away from a silicon substrate and operable to focus said laser beam onto said silicon substrate at an angle at least approximately 60 degrees from a line normal to said silicon substrate, wherein said focused laser beam at least partially reflects from said silicon substrate and diverges toward a first concave mirror;

said first concave mirror having a first mirror focal length and being disposed approximately two first mirror focal lengths away from said silicon substrate, said first concave mirror operable to focus said laser beam onto said silicon substrate, wherein said focused laser beam at least partially reflects from said silicon substrate and diverges toward a second concave mirror;

said second concave mirror having a second mirror focal length and being disposed approximately two second mirror focal lengths away from said silicon substrate, said second concave mirror operable to focus said laser beam onto said silicon substrate, said silicon substrate, said first concave mirror, and said second concave mirror together comprising a multi-pass Raman cell;

at least one lens operable to collect Raman light from said silicon substrate and provide an image of said Raman light to a spectrograph operable to separate said Raman light according to wavelength; and a filter operable to remove at least a portion of Rayleigh scattered light from said Raman light.

2. The Raman spectrometer of claim 1, wherein said laser source comprises a laser diode.

3. The Raman spectrometer of claim 2, wherein said laser diode comprises a grating-locked laser diode.

4. The Raman spectrometer of claim 3, wherein said angle is at least approximately 70 degrees.

5. The Raman spectrometer of claim 4, wherein said angle is at least approximately 80 degrees.

6. The Raman spectrometer of claim 3, wherein said filter comprises a holographic notch filter.

7. The Raman spectrometer of claim 6, wherein said holographic notch filter has an optical density of at least 5 for said Rayleigh scattered light.

8. The Raman spectrometer of claim 3, wherein said filter comprises an atomic vapor absorption filter.

9. The Raman spectrometer of claim 8, wherein said atomic vapor absorption filter comprises a rubidium absorption filter.

10. The Raman spectrometer of claim 3, further comprising a Dove prism operable to rotate said image of said Raman light.

11. The Raman spectrometer of claim 3, wherein said spectrograph further comprises a chilled CCD camera.

12. The Raman spectrometer of claim 11, wherein said chilled CCD camera is coupled to a programmed computer operable to analyze said Raman light.

13. The Raman spectrometer of claim 3, wherein said silicon substrate further comprises a layer of silicon dioxide operable to chemisorb a chemical species for analysis.

* * * * *